United States Patent [19]
Doherty

[11] Patent Number: 5,267,984
[45] Date of Patent: Dec. 7, 1993

[54] CONNECTOR FOR A MEDICAL TUBE

[76] Inventor: Darren Doherty, 2020 Carr La., #5, Sulphur, La. 70663

[21] Appl. No.: 789,923

[22] Filed: Nov. 12, 1991

[51] Int. Cl.$^5$ ............................................. A61M 25/00
[52] U.S. Cl. .................................. 604/283; 604/326; 604/905; 128/207.14
[58] Field of Search ............... 604/283, 326, 256, 905, 604/243; 128/207.14, 204.18

[56] References Cited

U.S. PATENT DOCUMENTS

| | | | |
|---|---|---|---|
| 4,076,285 | 2/1978 | Martinez | 604/905 X |
| 4,296,949 | 10/1981 | Muetterties et al. | 604/905 X |
| 4,369,991 | 1/1983 | Linder | 604/905 X |
| 4,826,486 | 5/1989 | Palsrok et al. | 604/905 X |
| 5,053,015 | 10/1991 | Gross | 604/243 X |

Primary Examiner—John D. Yasko
Attorney, Agent, or Firm—Keaty & Keaty

[57] ABSTRACT

The invention relates to a connector member for connecting adjacent portions of a medial tube to allow easy disengagement of the adjacent portions, when required. The connector has a hollow body with a central opening which allows to fit the connector over a portion of the medical tube and frictionally engage that portion. A pair of opposite gripping wings are carried by an exterior surface of the connector body, the gripping wings extending perpendicularly to the exterior surface. When disengaging the adjacent portions of the tube, a torque is applied to the gripping members and transmitted to the engaged portion of the medical tube until the adjacent portions are separated.

8 Claims, 1 Drawing Sheet

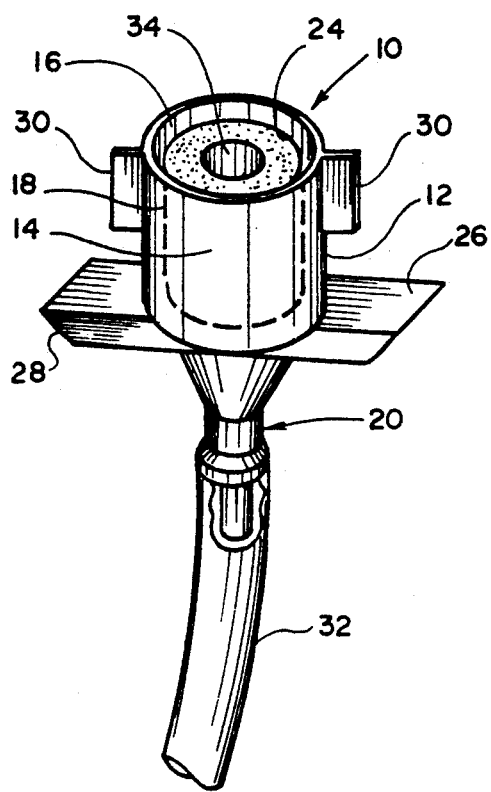
F I G. 1
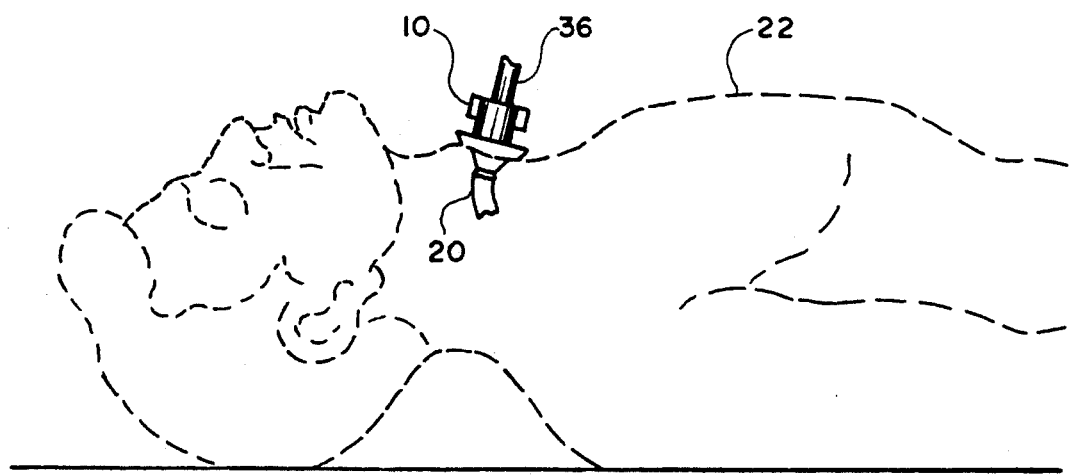
F I G. 2

CONNECTOR FOR A MEDICAL TUBE

BACKGROUND OF THE INVENTION

The present invention relates to a medical device, and more particularly to a connector for use with a medical tube, such as endotracheal tube and the like.

In many medical emergency cases there exists a need to establish a direct communication between an internal cavity of a patient and an exterior of the patient's body bypassing the normal pathways of breathing, food consumption, etc. In such cases an incision is made in a patient's throat, or other body portion, so that an endotracheal, or similar tube can be inserted through the incision to allow lung ventilation bypassing mouth and nose.

After a pre-determined period of time the tube is removed an the incision heals, closing the artificially made opening. However, in some cases, the portion of the tube which extends into the trachea, stays in place, while an exterior portion of the tubing is replaced, cleaned, etc.

It should be also noted that the tube itself is usually a combination of a number of mutually connected parts, which fittingly engage each other and can be easily detached from each other, when necessary.

It was observed that it may be extremely inconvenient to disengage two portions of the tube which are immediately adjacent the area of connection between the exterior part of the tube and the inner part of the tube. These portions are frictionally engaged with each other, and the attending person simply pulls apart those portions, which force can impart undesirable painful sensation in the patient.

The present invention contemplates provision of a special connector which would allow easy disengagement of the tube portions, when necessary.

SUMMARY OF THE INVENTION

It is therefore an object of the present invention to provide a connector for a medical tube.

It is another object of the present invention to provide a connector which is simple to use and easy to manufacture.

It is a further object of the present invention to provide a connector for a medical tube which allows easy disengagement of tube portions, when required.

These and other objects of the present invention are achieved through provision of a medical tube connector which comprises a tubular body having a central opening extending therethrough. The connector has a continuous exterior wall which carries a pair of diametrically positioned engaging wings. The wings extend perpendicularly to a central axis of the tubular body to a distance sufficient to allow gripping of the wings by hand, thereby facilitating a turning action of the connector when two portions of the tube are disengaged from each other.

BRIEF DESCRIPTION OF THE DRAWINGS

Reference will now be made to the drawings, wherein like parts are designated by like numerals, and wherein FIG. 1 is a perspective view of the device of the present invention mounted on a portion of a medical tube.

FIG. 2 is a schematic view illustrating position of the device of the present invention in relation to a patient's body.

DETAILED DESCRIPTION OF THE PREFERRED EMBODIMENT

Referring to the drawings in more detail, numeral 10 designated the connector device in accordance with the present invention. The connector 10 comprises a tubular body 12, having a continuous exterior wall 14 and a central opening 16 extending axially through the length of the body 12.

The opening 16 is conveniently sized and shaped to fit over a portion 18 of a medical tube 20 which extends outwardly in relation to the patient's body 22.

If desired, an annular wall 24 which defines the opening 16 can be provided with spaced-apart grooves (not shown) which facilitate frictional engagement of the connector 10 with the tube portion 18.

The length of the body 12 can be substantially equal to, slightly smaller, or slightly greater than the length of the tube portion 18. It is preferred, though, that the body 12 contact an outer surface 26 of a cross member 28 of the medical tube 20, so as to sit against that surface.

The bottom surface of the cross member 28 usually contacts the body of the patient in an area surrounding the incision.

Extending outwardly form the exterior wall 14 of the body 12 are a pair of gripping members, or wings 30, which are narrow plate-like extensions formed either integrally with the wall 14 or in a rigid engagement thereto.

The wings 30 can have rectangular, oval or any other desired shape, but should have a size sufficient enough to be gripped by fingers of the attending personnel. The wings 30 are used for applying torque to the body 12 when disengaging an exterior portion 18 of the tube 20 from an interior portion 32 thereof.

As can be seen in FIG. 1, the wings 30 extend in diametrically opposite directions form the annular wall 14 at a substantially right angle to the longitudinal axis of the body 12 and to the wall 14.

The wins 30, as well as the body 12 can be made of plastic, or any other suitable material strong enough to withstand a twisting, turning force applied to the wings 30 and transmitted to the body 12 during disengagement of the tube portions.

Although not shown in great detail, it is presumed that an oxygen-supplying tubing 36 (schematically shown in FIG. 2) is fitted within an opening 34 formed in the portion 18 of the tube 20, so as to connect the tube 20 with the necessary source of oxygen.

When in use, the device 10 is positioned as a connecting member at a portion of the tube 20 immediately adjacent entry of the tube 20 into the patient's body. When it becomes necessary, for some purpose, to disengage the exterior portion 18 of the tube 20 from the inner portion 32 thereof, an attending person grips the connector 10 by wings 30 and turns the body 12 until the portion 18 is disengaged from the portion 32.

The use of the connector 10 allows to apply a turning force when disengaging those two members as compared to the usual pulling force applied to a conventionally used cylindrical connector without any gripping members. As a result, a possibility of hurting a patent is substantially reduced.

While the connector device 10 was described and illustrated in use with an endotracheal tube, it will be appreciated that the device 10 can be used with other medical tubes in situations, where application of rotating force, instead of a pulling force is recommended.

Many changes and modifications can be made in a design of the present invention without departing form the spirit thereof. I, therefore, pray that my rights to the present invention be limited only by the scope of the appended claims.

I claim:

1. A connector device for connecting adjacent portions of a medical tube, the device comprising:

a substantially hollow connector body having a protrusion free inner wall for forming a female connection by fitting over a portion of a medical tube and frictionally engaging therewith; said body is a tubular body having a central opening extending therethrough, said opening being sized and shaped to frictionally receive a portion of a medical tube therein and a gripping means carried by an exterior surface of the body for facilitating manual gripping of the connector device when applying torque to the body in order to disengage adjacent portions of a medical tube, said gripping means comprising a pair of narrow gripping members extending in opposite directions from the body in a substantially co-planar relationship to a longitudinal section of the body.

2. The device of claim 1 wherein said gripping means extend outwardly form said exterior surface of the connector body in a substantially perpendicular relationship thereto.

3. The device of claim 2, wherein each of said gripping members comprises a plate having an elongated edge securely attached to the body and oriented in a substantially parallel relationship to a longitudinal axis of the body and a gripping surface extending in a co-planar relationship to said edge, each of said gripping members adapted to receive torque applied to said gripping surface during disengagement of the medical tube portions.

4. A connector device for connecting adjacent portions of a medical tube, the device comprising:

a substantially hollow tubular body having a central opening extending therethrough, the opening being sized and shaped to fit over a portion of a medical tube, such that an annular wall defining the central opening frictionally engages that portion of the medical tube, said annular wall having a protrusion-free surface; and a gripping means carried by an exterior wall of the tubular body and extending substantially perpendicularly to the exterior wall, said gripping means comprising a pair of opposite gripping members, each gripping member having a narrow elongated edge securely attached to the exterior wall in a parallel relationship to a longitudinal axis of the body and a gripping surface extending in a co-planar relationship to a longitudinal section of the body.

5. The device of claim 4, wherein said gripping members are positioned diametrically opposite each other.

6. The device of claim 5, wherein said gripping members are adapted to receive torque applied to the tubular body when disengaging adjacent portions of the medical tube.

7. A method of disengaging adjacent portions of a medical tube, comprising the following steps:

providing a connector body having a central opening extending therethrough, the opening being sized and shaped to fit over a first portion of the medical tube, an annular wall defining said opening being protrusion free, while said connector body is frictionally fitted over the first portion of the medical tube;

providing gripping means on an exterior surface of the connector body;

gripping said gripping means by one hand, while holding a second, adjacent portion of the medical tube by another hand;

applying torque to the gripping means; and transmitting said torque to the first portion of the medical tube until the first portion of the medical tube is disengaged from the second portion of the medical tube.

8. The method of claim 7, wherein said gripping means comprise a pair of opposite gripping members extending outwardly in a substantially perpendicular relationship to the exterior surface of the connector body, each of said gripping members comprising a narrow plate having an elongated edge securely attached to the connector body in a parallel relationship to a longitudinal axis of the connector body and a gripping surface which is oriented in a co-planar relationship to a longitudinal section of the connector body.

* * * * *